United States Patent
Lark et al.

(10) Patent No.: US 12,402,890 B2
(45) Date of Patent: Sep. 2, 2025

(54) MEDICAL CUTTING DEVICES HAVING A WORKING BLADE BODY WITH STATIC COMPONENTS AND RELATED METHODS OF USE

(71) Applicant: Innovations 4 Surgery, LLC, Chapel Hill, NC (US)

(72) Inventors: Robert K. Lark, Chapel Hill, NC (US); Edward C. Skolnick, Denville, NJ (US); Antoine R. Kaeslin, Bethel, CT (US)

(73) Assignee: Innovations 4 Surgery, LLC, Chapel Hill, NC (US)

( * ) Notice: Subject to any disclaimer, the term of this patent is extended or adjusted under 35 U.S.C. 154(b) by 382 days.

(21) Appl. No.: 18/087,766

(22) Filed: Dec. 22, 2022

(65) Prior Publication Data

US 2023/0190304 A1     Jun. 22, 2023

Related U.S. Application Data

(60) Provisional application No. 63/292,438, filed on Dec. 22, 2021.

(51) Int. Cl.
*A61B 17/14*     (2006.01)
*A61B 17/00*     (2006.01)
(Continued)

(52) U.S. Cl.
CPC ...... *A61B 17/142* (2016.11); *A61B 17/32002* (2013.01); *A61B 17/320068* (2013.01); *A61B 2017/00101* (2013.01); *A61B 2017/00115* (2013.01); *A61B 2017/00123* (2013.01); *A61B 2017/320075* (2017.08); *A61B 2017/564* (2013.01); *A61B 2217/007* (2013.01)

(58) Field of Classification Search
CPC ...... A61B 17/142; A61B 2017/320028; A61B 2017/32002; A61B 2017/320068; A61B 2017/320077
See application file for complete search history.

(56) References Cited

U.S. PATENT DOCUMENTS

| | | | |
|---|---|---|---|
| 4,008,720 A | 2/1977 | Brinckmann et al. | |
| 5,087,261 A | 2/1992 | Ryd et al. | |

(Continued)

FOREIGN PATENT DOCUMENTS

| | | | | |
|---|---|---|---|---|
| DE | 202008017023 U1 | * | 4/2009 | ............. A61B 17/14 |
| DE | 102008062880 A1 | * | 6/2010 | ............. A61B 17/14 |

*Primary Examiner* — Matthew J Lawson
(74) *Attorney, Agent, or Firm* — Olive Law Group, PLLC

(57) ABSTRACT

Medical cutting device having a working blade body with static components and related methods of use are disclosed. According to an aspect, a cutting device includes a working blade body having a top surface and a bottom surface. The working blade body defines a plurality of apertures extending between the top surface and the bottom surface. Further, the cutting device includes a plurality of static components each having a top portion and a bottom portion. Each static component is associated with one of the apertures and has a middle portion that is between the top portion and the bottom portion and positioned within the associated aperture. The top portion and the bottom portion extend past the top surface and the bottom surface, respectively, of the working blade body.

15 Claims, 9 Drawing Sheets

(51) Int. Cl.
*A61B 17/32* (2006.01)
*A61B 17/56* (2006.01)

(56) References Cited

U.S. PATENT DOCUMENTS

| | | | |
|---|---|---|---|
| 5,122,142 A | 6/1992 | Pascaloff | |
| 5,188,102 A | 2/1993 | Idemoto et al. | |
| 5,261,922 A | 11/1993 | Hood | |
| 5,728,130 A | 3/1998 | Ishikawa | |
| 6,379,371 B1 | 4/2002 | Novak | |
| 6,443,969 B1 | 9/2002 | Novak | |
| 8,343,178 B2 | 1/2013 | Novak | |
| 8,348,880 B2 | 1/2013 | Messerly et al. | |
| D680,218 S | 4/2013 | Darian | |
| 9,320,528 B2 | 4/2016 | Voic | |
| 9,554,809 B2 | 1/2017 | Lark | |
| 10,238,415 B2 | 3/2019 | Naono | |
| 10,702,296 B2 | 7/2020 | Boudreaux | |
| 2003/0176867 A1* | 9/2003 | Long | A61B 17/142 606/79 |
| 2003/0204199 A1 | 10/2003 | Novak | |
| 2005/0273127 A1 | 12/2005 | Novak | |
| 2008/0009848 A1 | 1/2008 | Paraschiv | |
| 2013/0204256 A1* | 8/2013 | Wang | B23D 61/006 606/82 |
| 2013/0204285 A1 | 8/2013 | Gouery | |
| 2015/0005771 A1 | 1/2015 | Voic | |
| 2015/0088137 A1 | 3/2015 | Manna | |
| 2016/0089155 A1 | 3/2016 | Lark | |
| 2017/0056052 A1 | 3/2017 | Dickerson | |
| 2017/0340339 A1 | 11/2017 | Madan | |
| 2017/0340344 A1 | 11/2017 | Boudreaux | |
| 2017/0340345 A1 | 11/2017 | Yates | |
| 2018/0344346 A1 | 12/2018 | Naono | |
| 2019/0240751 A1* | 8/2019 | Skolnick | A61B 17/142 |
| 2020/0001494 A1* | 1/2020 | Gisler | A61B 17/142 |
| 2021/0113215 A1* | 4/2021 | Gisler | A61B 17/1637 |
| 2021/0121195 A1 | 4/2021 | Richards | |
| 2021/0186525 A1 | 6/2021 | Lark | |
| 2023/0190327 A1* | 6/2023 | Lark | A61B 17/320068 606/167 |
| 2024/0307070 A1* | 9/2024 | Uhri | A61B 17/142 |

* cited by examiner

MEDICAL CUTTING DEVICES HAVING A WORKING BLADE BODY WITH STATIC COMPONENTS AND RELATED METHODS OF USE

CROSS REFERENCE TO RELATED APPLICATIONS

This application claims priority to U.S. Provisional Patent Application No. 63/292,438, filed Dec. 22, 2021, and titled MEDICAL DEVICES AND RELATED METHODS FOR TRANSFORMING BONE, OTHER TISSUE, OR MATERIAL, the content of which is incorporated herein by reference in its entirety.

This application is related to U.S. Nonprovisional patent application Ser. No. 18/087,715, filed Dec. 22, 2022, and titled MEDICAL CUTTING DEVICES WITH A STATIC CASING AND A BLADE WORKING BODY OF GREATER WIDTH AND RELATED METHODS.

This application is related to U.S. Nonprovisional patent application Ser. No. 18/087,727, filed Dec. 22, 2022, and titled MEDICAL CUTTING DEVICES WITH STATIC COMPONENTS HAVING TEMPERATURE SENSORS AND RELATED METHODS.

This application is related to U.S. Nonprovisional patent application Ser. No. 18/087,741, filed Dec. 22, 2022, and titled MEDICAL CUTTING DEVICES WITH COOLANT MODULES AND CHANNELS AND ASSOCIATED METHODS.

This application is related to U.S. Nonprovisional patent application Ser. No. 18/087,749, filed Dec. 22, 2022, and titled MEDICAL CUTTING DEVICES HAVING A BLADE WORKING BODY THAT DEFINES AN OPENING FOR EMITTING COOLANT THEREFROM AN RELATED METHODS.

TECHNICAL FIELD

The presently disclosed subject matter relates generally to medical devices. Particularly, the presently disclosed subject matter relates to medical cutting device having a working blade body with static components and related methods of use.

BACKGROUND

Traditional surgical saws, such as oscillating saws and reciprocating saws, allow users to cut bones (i.e. perform osteotomies) of relatively large diameters, such as the tibia and femur. These types of surgical saws, however, which are similar in many ways to the toothed saws used to cut wood, metal, and plastic, have significant disadvantages with respect to a patient's well-being. Because surgical saws utilize rapid motion of the saw blade to cut biological tissues, such as bone and cartilage, a significant amount of heat is generated along the blade and particularly at the blade and bone interface. This can be harmful to the patient since prolonged exposure of bone cells to temperatures at or in excess of 47° C. leads to necrosis of those osteocytes. Another disadvantage of these oscillating and reciprocating bone saws is that they produce uneven cuts, preventing ideal realignment and reduction of the osteotomy gap, which is detrimental to efficient healing of the bone. Oscillating and, in particular, reciprocating bone saws, which utilize a number of sharpened teeth along their cutting edges, can tear neighboring soft tissues that are inadvertently caught in the serrations of the rapidly moving blade. Tearing of these soft tissues leads to significant blood loss and potential nerve damage, which undoubtedly hampers the health of the patient.

Traditional oscillating and reciprocating bone saws have employed a variety of different measures to address these disadvantages. With respect to the generation of excessive heat, these surgical saws can utilize irrigation systems to flush the surgical site near the blade and bone interface. These irrigation systems can be separate, requiring an additional device at the surgical site, or integrated. Although effective at flushing a surgical site of unwanted sources of added friction, these irrigation systems are relatively ineffective at actually cooling the blade at the blade and bone interface. For example, one design for a surgical saw that incorporates a means for irrigation comprises a channel between otherwise parallel portions of a saw blade through which fluid can flow out into the surgical site (See U.S. Pat. No. 5,087,261). This channel, though, can be easily compacted with surgical debris, rendering the integrated irrigation system unusable. In addition, providing a channel between parallel portions of the saw blade necessarily increases the likelihood of a wider, more uneven cut. Other designs for an oscillating bone saw include outlets along the blade's edge to facilitate irrigation along the blade and bone interface (See U.S. Pat. Nos. 4,008,720 and 5,122,142). However, these channels can be similarly compacted with surgical debris, rendering them useless. More so, channels along the very blade edge result in a blade edge that is not continuous, which reduces the cutting efficiency of the blade. Despite any potential efficacy in flushing a site of surgical debris, these systems do very little to actually cool the very blade edge, specifically at the blade and bone interface. Additionally, having copious amounts of irrigation fluid in the surgical site can hamper the surgeon's ability to visualize important anatomic structures.

Just as with saws used to cut wood, metal, and plastic, a user can avoid rough or uneven cuts by using a saw blade that incorporates more teeth along the edge of the blade and/or teeth having differing angles. While this can produce a relatively finer cut, the resulting cut still leaves much to be desired in terms of producing smooth, even bone surfaces. Cutting guides, which help to stabilize the blade and keep it on a prescribed plane, are often utilized during an osteotomy to improve the precision of the cut. Still, the improvement is not substantial enough to consider these measures a long-term solution with respect to producing smooth bone cuts. In fact, adding teeth or guiding the blade edge have little effect in preventing inadvertent tearing of neighboring soft tissues. Although efforts are taken to protect soft tissues from damage and prevent significant blood loss, the inherently close confines typical in performing any osteotomy make it extremely difficult to completely eliminate such damage, especially to those tissues that are unseen or positioned beneath the bone being cut. This is compounded by the fact that the saw blades used with many oscillating and reciprocating bone saws are relatively large.

A variety of ultrasonic surgical devices are now utilized in a number of surgical procedures, including surgical blades that are capable of cutting biological tissues such as bone and cartilage. These types of saw blades are powered by high-frequency and high-amplitude sound waves, consequent vibrational energy being concentrated at the blade's edge by way of an ultrasonic horn. Being powered by sound waves, neighboring soft tissues are not damaged by these types of blades because the blade's edge effectively rebounds due to the elasticity of the soft tissue. Thus, the significant blood loss common with use of traditional bone saws is prevented. In addition, significantly more precise cuts are possible using ultrasonic bone cutting devices, in part, because the blade's edge does not require serrations. Instead, a continuous and sharpened edge, similar to that of a typical scalpel, enables a user to better manipulate the surgical device without the deflection caused by serrations, which is common when using oscillating and reciprocating bone saws. Although ultrasonic cutting blades are advantageous in that they are less likely to tear neighboring soft tissues and more likely to produce relatively more even cuts, these types of blades still generate considerable amounts of heat.

As with traditional bone saws, separate or integrated irrigation systems are often utilized in order to flush the surgical site and generally provide some measure of cooling effect to the blade. However, many of these blades suffer from the same disadvantages as traditional bone saws that have tried to incorporate similar measures. For example, providing openings along the blade's edge through which fluid flows introduces voids in the cutting edge, thereby inhibiting the cutting efficiency of the blade (See U.S. Pat. No. 5,188,102). In addition, these fluid openings can be readily compacted with surgical debris, rendering them useless for their intended function. In other blade designs, the continuity of the blade is maintained and a fluid outlet is positioned just before the blade's edge (See U.S. Pat. No. 8,348,880). However, this fluid outlet merely irrigates the surgical site since it is positioned too far from the blade and bone interface to actually provide the necessary cooling effect. Also, it irrigates only one side of the blade. Another design for an ultrasonic cutting device, which claims to cool the blade, incorporates an irrigation output located centrally along the longitudinal axis of the blade (See U.S. Pat. No. 6,379,371). A recess in the center of the blade tip allows fluid to flow out of this output and toward the blade's edge, flow that is propelled by a source of pressure. However, the positioning of this irrigation output within the contour of the blade tip results in a bifurcation or splitting of the irrigation flow, such splitting tending to distribute fluid at an angle away from the blade's edge. Mentioned above, the excessive heat generated using any cutting blade, including an ultrasonic cutting blade, is focused most significantly at the blade and bone interface. This example for an ultrasonic blade with cooling capabilities, then, does little to actually cool the blade at the blade and bone interface, but instead serves merely to flush debris from the surgical site. Again, having copious amounts of irrigation fluid in the surgical site can hamper the surgeon's ability to visualize important anatomic structures. Furthermore, this ultrasonic blade is not well-suited to cutting large cross-sections of bone and is used almost exclusively in spine, oral or maxillofacial surgeries, which involve cutting of small bones.

Even assuming that any of the irrigation systems incorporated into the various bone saws provide some measure of cooling, thermal burning of both neighboring soft tissues and bone surfaces remains a significant problem. Because the working surface of the blade also moves rapidly, considerable heat is generated along its length, too. The dynamic motion of the surf contacts neighboring soft tissues, potentially burning them. With respect to an osteotomy, as the blade passes through the cross-section of bone, the freshly-cut bone surfaces remain in constant and direct contact with the rapidly vibrating shaft of the blade. As a result, it is not uncommon to burn the bone, produce smoke and, more importantly, kill osteocytes. In fact, simply lengthening an ultrasonic blade to accommodate large cross-sections of bone tissue, for example, increases the surface area through which heat can transfer and, thus, is avoided by manufacturers of these types of blades. While irrigation directed specifically toward the blade's leading edge may provide some measure of cooling at the blade and bone interface, irrigation alone is insufficient in trying to avoid prolonged exposure of bone tissue, for example, to temperatures in excess of 47° C. Therefore, there remains a need for a surgical device that is capable of cutting bones with large cross-sections, such as the femur, while maintaining a working temperature along the entirety of the blade shaft that does not inhibit proper healing of the bone tissue.

In some applications, there is a need to Protecting the viability of the bone can allow for the use of a cementless implant to allow for bone in-growth/osteointegration.

For at least the aforementioned reasons, there is a need for improved surgical devices and techniques.

BRIEF DESCRIPTION OF THE DRAWINGS

Figure 1:
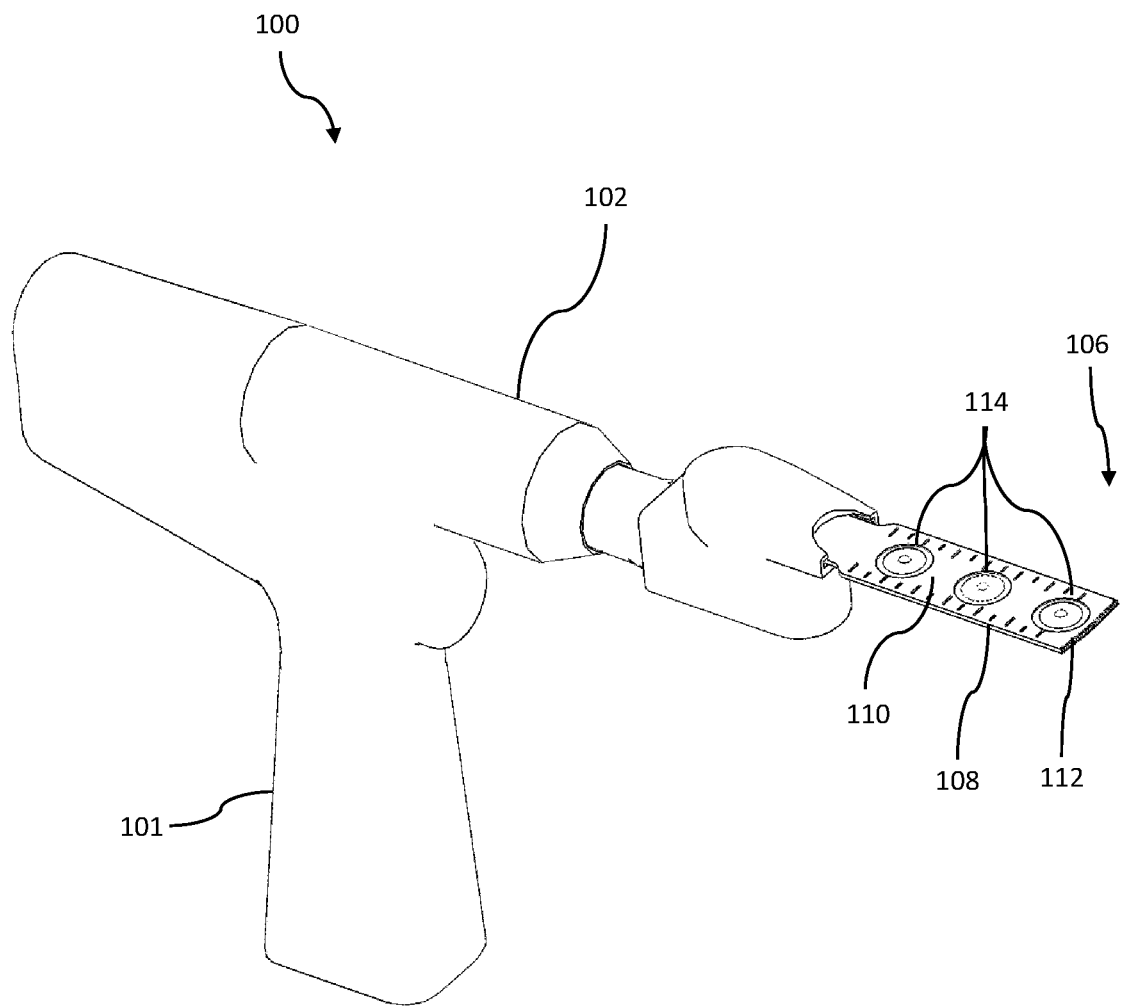
Figure 2:
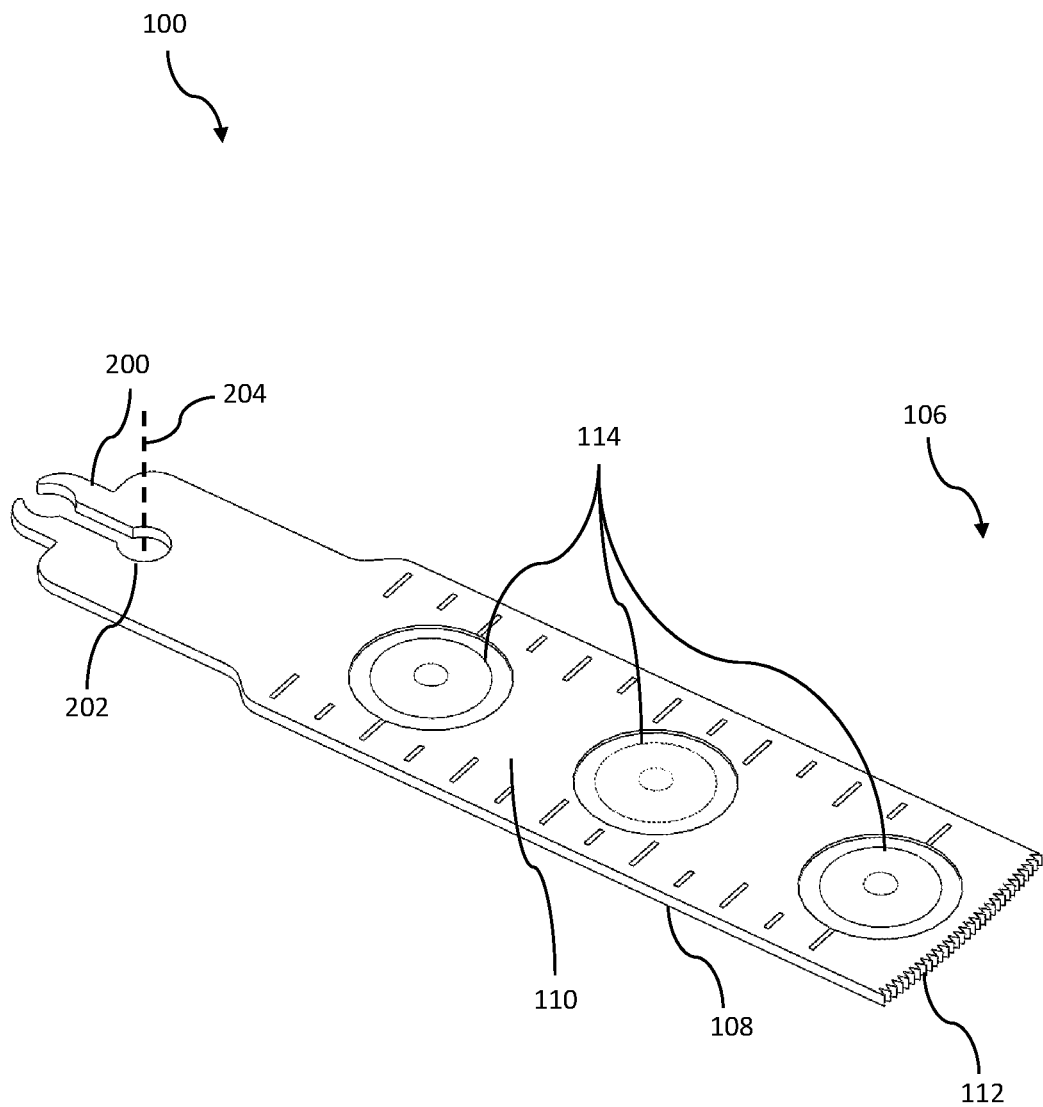
Figure 3:
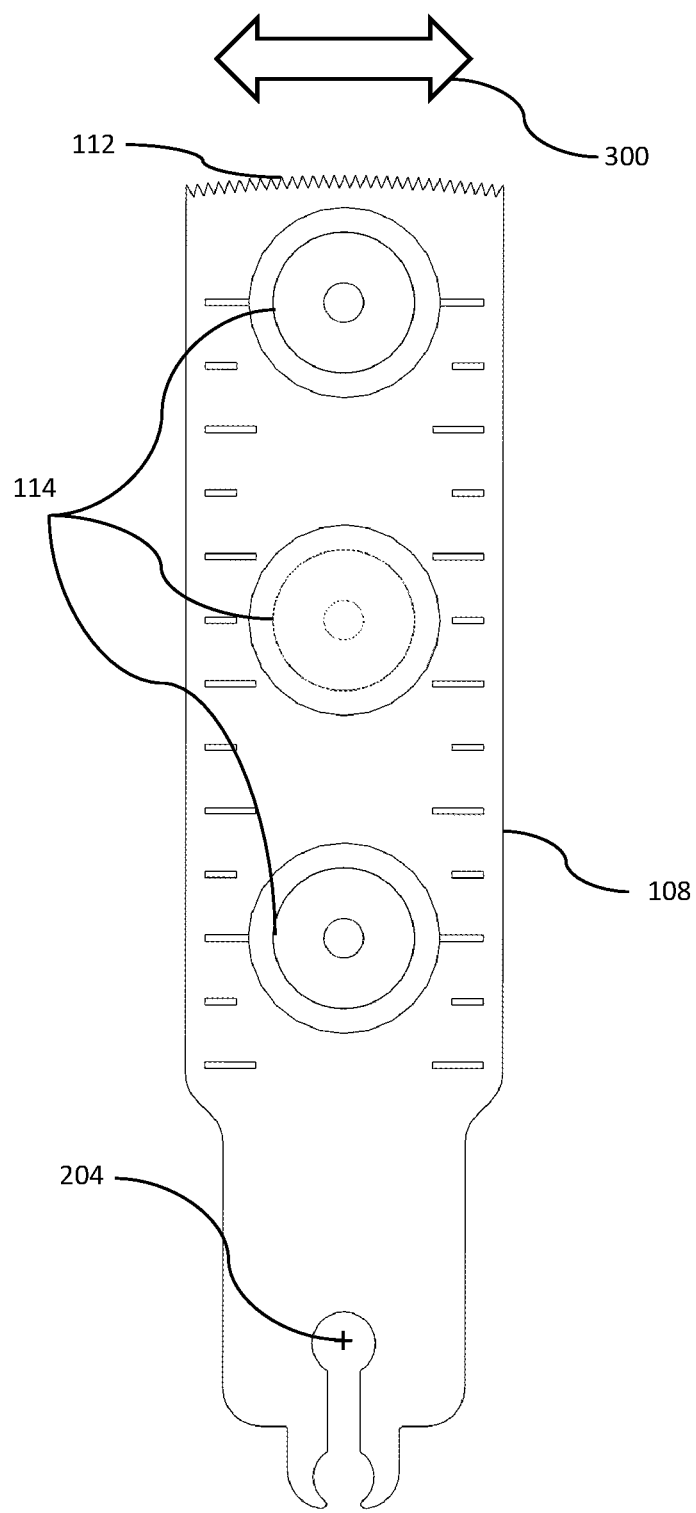
Figure 4:
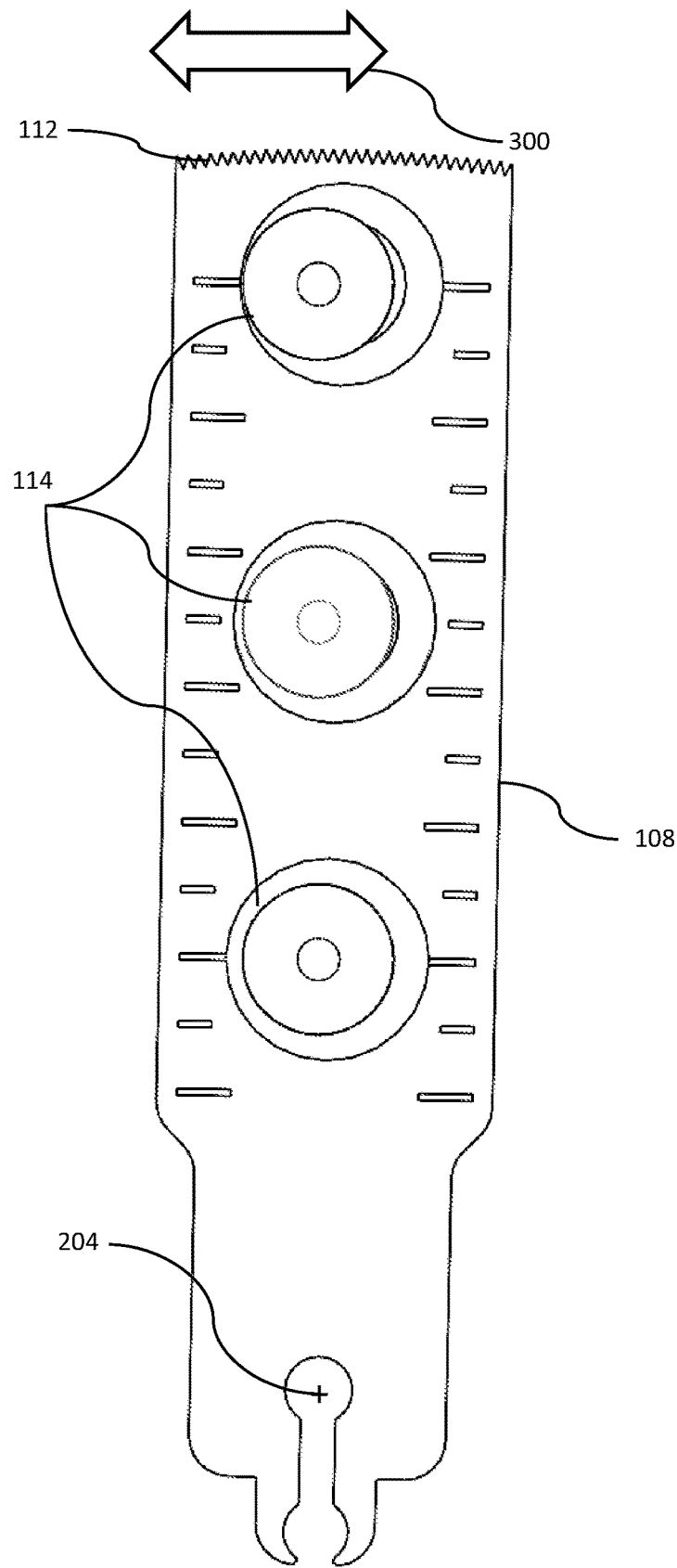
Figure 5:
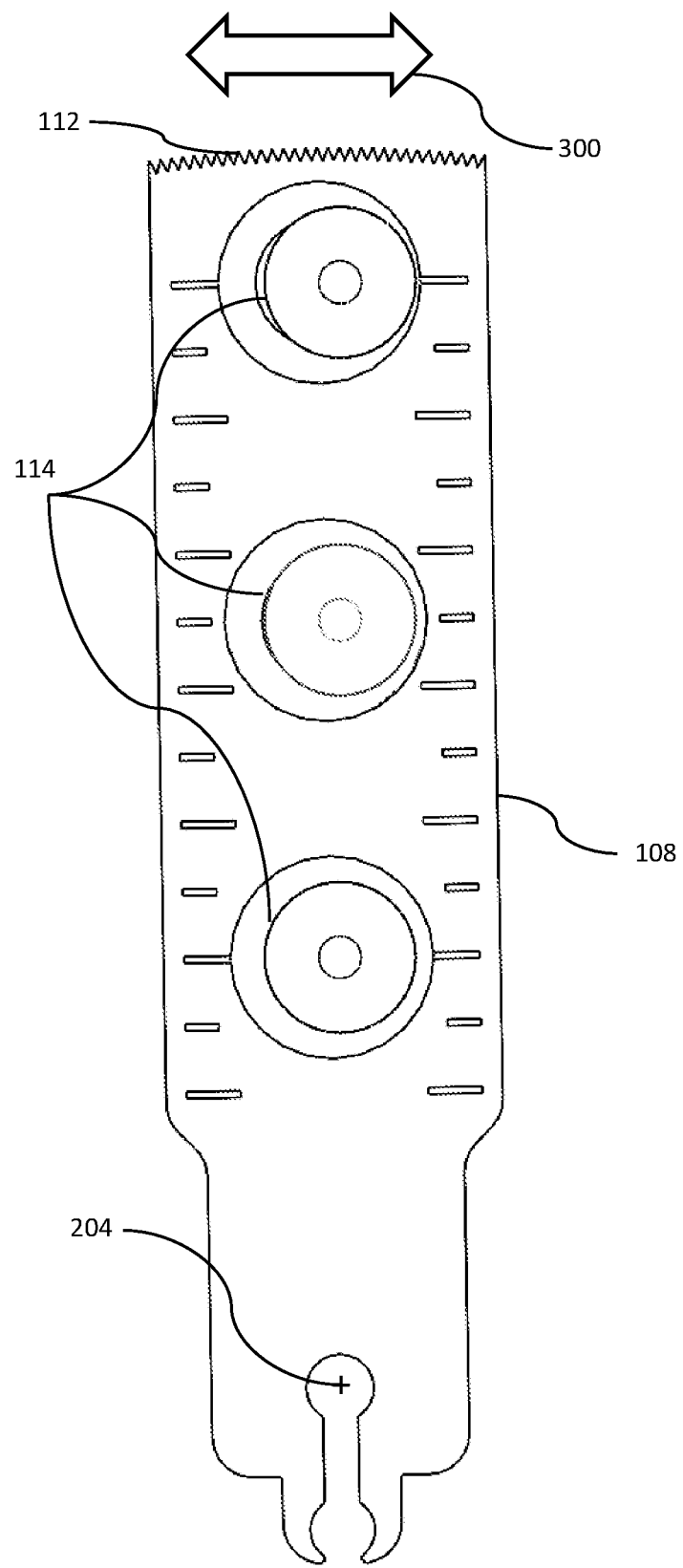
Figure 6:
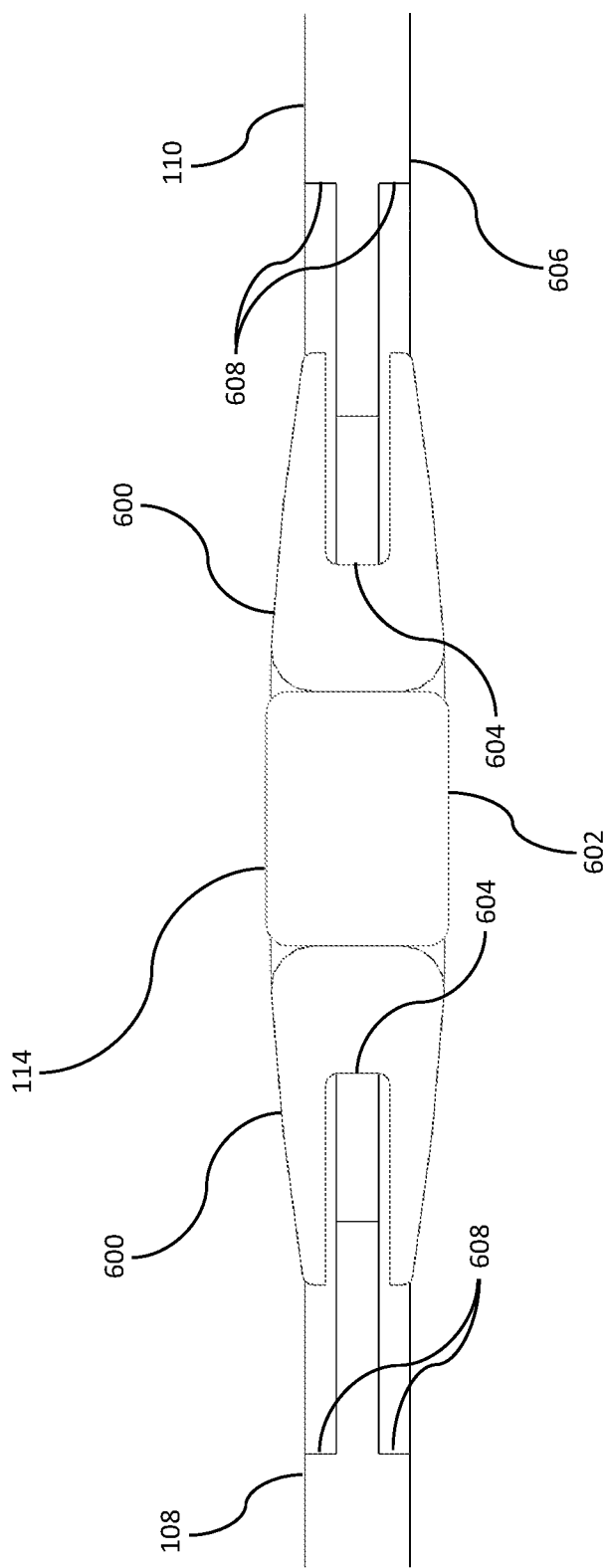
Figure 7:
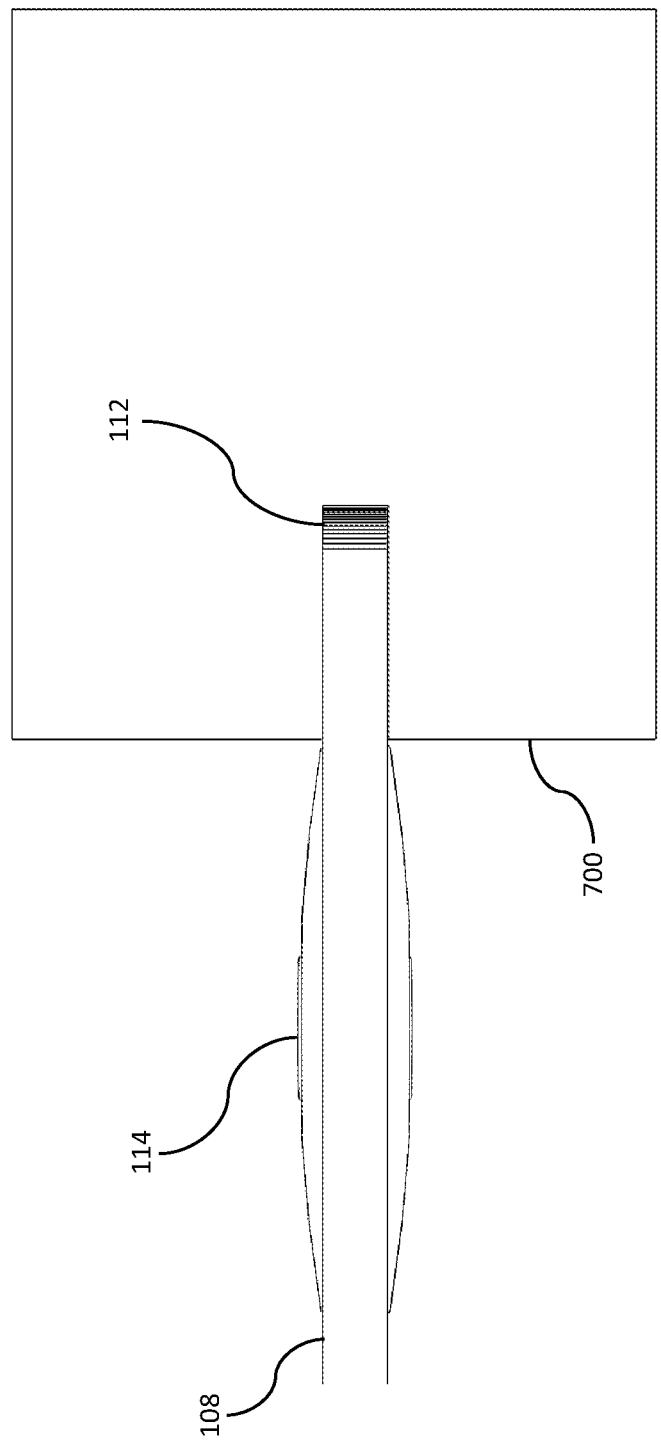
Figure 8:
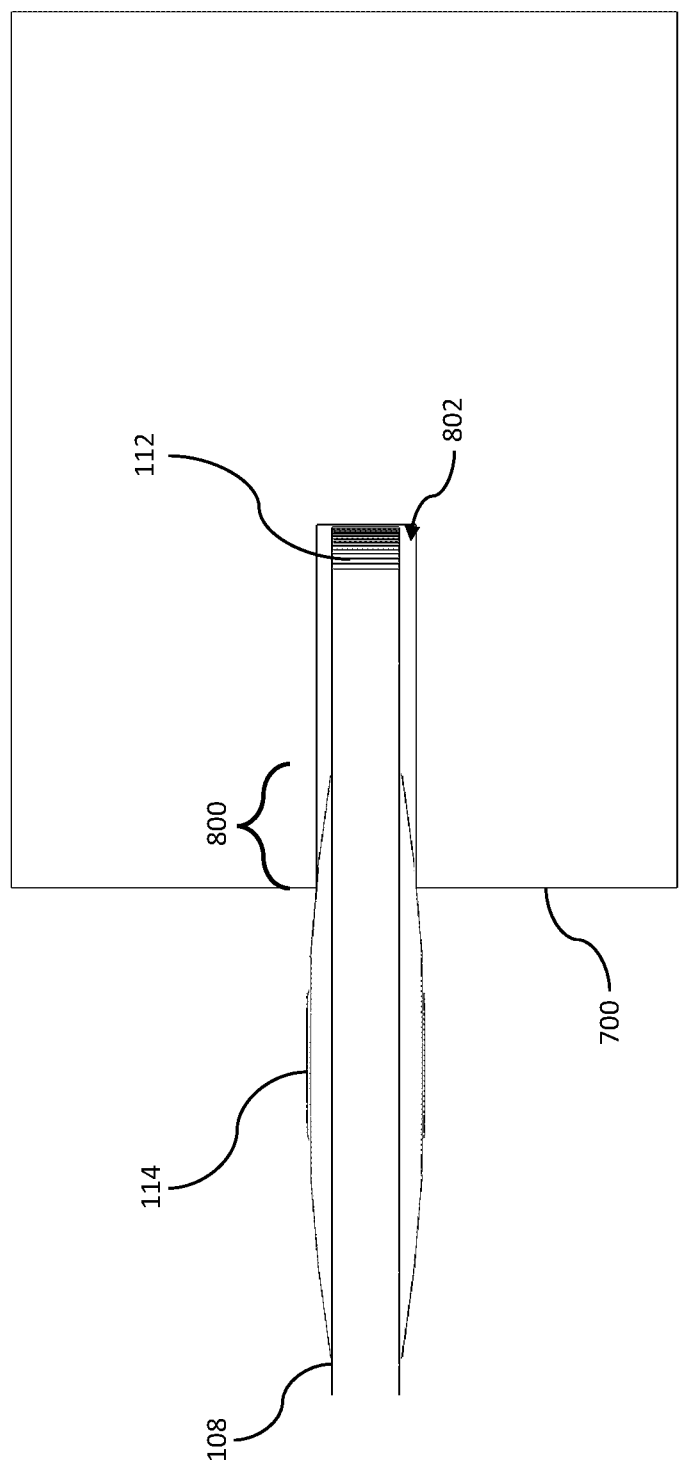
Figure 9:
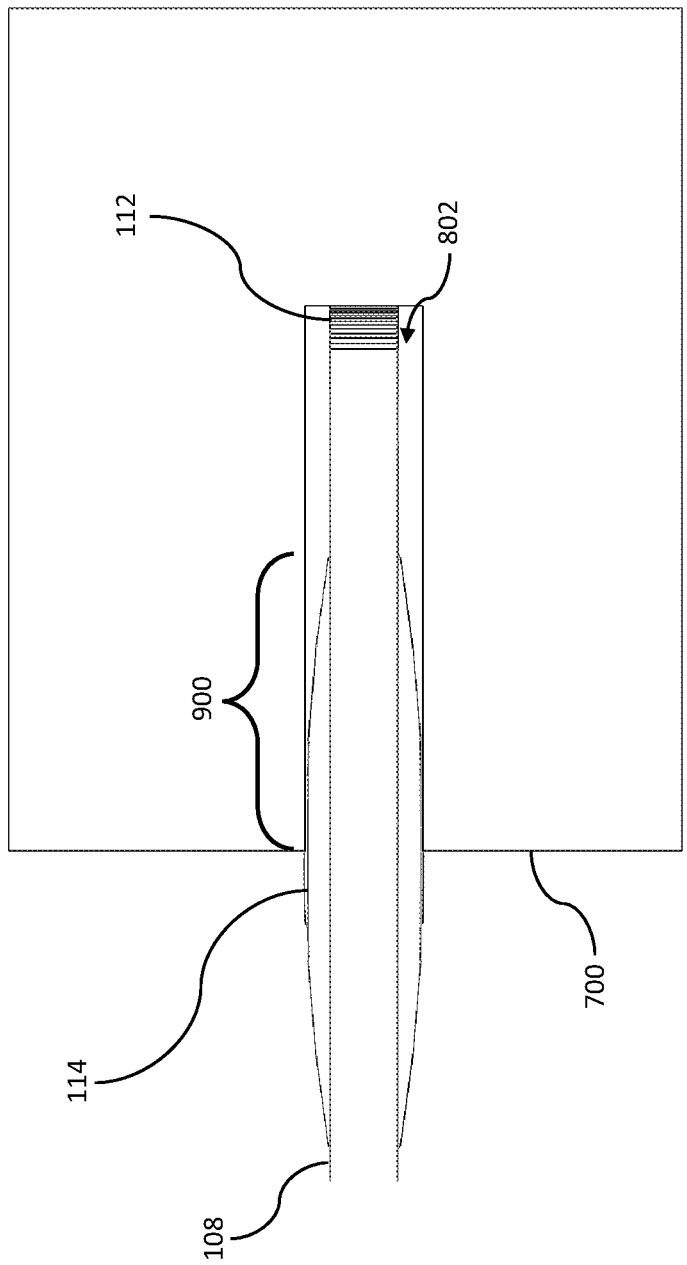

Having thus described the presently disclosed subject matter in general terms, reference will now be made to the accompanying Drawings, which are not necessarily drawn to scale, and wherein:

FIG. 1 is a top perspective view of a cutting device in accordance with embodiments of the present disclosure;

FIG. 2 is a top perspective view of the blade working body and static components shown in FIG. 1;

FIGS. 3-5 depict tops views of the blade working body shown in FIGS. 1 and 2 at different positions of operation for cutting or transforming a material;

FIG. 6 illustrates a side, cross-sectional view of a portion of the working blade body and one static component as shown in FIGS. 1-5; and FIGS. 7-9 illustrate side views of a blade working body at different positions cutting into a material according to embodiments of the present disclosure.

SUMMARY

The presently disclosed subject matter relates to medical cutting device having a working blade body with static components and related methods of use. According to an aspect, a cutting device includes a working blade body having a top surface and a bottom surface. The working blade body defines a plurality of apertures extending between the top surface and the bottom surface. Further, the cutting device includes a plurality of static components each having a top portion and a bottom portion. Each static component is associated with one of the apertures and has a middle portion that is between the top portion and the bottom portion and positioned within the associated aperture. The top portion and the bottom portion extend past the top surface and the bottom surface, respectively, of the working blade body.

According to another aspect, a method includes providing a cutting device. The cutting device has a working blade body with static components and related methods of use. According to an aspect, a cutting device includes a working blade body having a top surface and a bottom surface. The working blade body defines a plurality of apertures extending between the top surface and the bottom surface. Further, the cutting device includes a plurality of static components each having a top portion and a bottom portion. Each static component is associated with one of the apertures and has a middle portion that is between the top portion and the bottom portion and positioned within the associated aperture. The top portion and the bottom portion extend past the top surface and the bottom surface, respectively, of the working blade body. The method also includes applying a force to the working blade body for cutting a material.

DETAILED DESCRIPTION

The following detailed description is made with reference to the figures. Exemplary embodiments are described to illustrate the disclosure, not to limit its scope, which is defined by the claims. Those of ordinary skill in the art will recognize a number of equivalent variations in the description that follows.

Articles "a" and "an" are used herein to refer to one or to more than one (i.e. at least one) of the grammatical object of the article. By way of example, "an element" means at least one element and can include more than one element.

"About" is used to provide flexibility to a numerical endpoint by providing that a given value may be "slightly above" or "slightly below" the endpoint without affecting the desired result.

The use herein of the terms "including," "comprising," or "having," and variations thereof is meant to encompass the elements listed thereafter and equivalents thereof as well as additional elements. Embodiments recited as "including," "comprising," or "having" certain elements are also contemplated as "consisting essentially of" and "consisting" of those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a range is stated as between 1%-50%, it is intended that values such as between 2%-40%, 10%-30%, or 1%-3%, etc. are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

As referred to herein, the term "cutting device" can be any suitable component movable for cutting into or generally transforming a material (e.g., bone). The cutting device can include a blade that operates through large or small (e.g., vibrations) mechanical motion. The motion can be in a specific direction(s). For example, the cutting device can be moved in an oscillating manner, flexing, bending, rotating, torsionally, longitudinally, and the like.

FIG. 1 illustrates a top perspective view of a cutting device 100 in accordance with embodiments of the present disclosure. Referring to FIGS. 1-4, the cutting device 100 includes handle 101 and a housing 102. Although these components are not shown in FIG. 1, the housing 102 may contain in an interior space therein for components, such as any suitable transducer or motor, to produce a desired mechanical motion with a cutting end, generally designated 106. It is noted that in this example the device 100 is described as being an oscillating saw blade, but it may alternatively be of any other suitable type (e.g., such as an ultrasonic transducer driving the blade through piezoelectric elements and smaller vibrations). The oscillating motor, which may be suitably powered to produce motion through the working surface of the blade to its blade edge, can be operatively attached to an end of a blade working body 108 that is closest to the housing 102. Oscillatory motion produced by the transducer/motor can propagate along a main body of the blade working body 108 towards an end of the blade working body 108 that opposes the end of the blade working body 108 that is attached to the oscillatory transducer/motor. It is noted that any other suitable motion may be produced alternative to mechanical oscillations such as those produced by traditional bone saws (e.g., such as those produced by ultrasonic cutting devices that use smaller scale vibrations). A static insert can be stationary or at least substantially stationary with respect to a source of movement since its motion is decoupled from that of the blade working body. The air gap present created by the static insert 114 can reduce transfer of energy from the blade working body 108 and, thus, heat to the surrounding bone. It is noted that the static insert may be made of any suitable insulative material, such as ceramic/polymer/rubber or any other suitable medical grade material, for preventing or minimizing heat transfer to the bone. Air can be present around the static insert and/or blade.

The cutting end 106 can be a blade tip configured to cut, ablate, abrade or otherwise transform, for example, bone or other tissue. The cutting end 106 includes a top surface 110 and an opposing bottom surface (not shown in FIG. 1). The cutting end 106 defines at least one blade edge 112. In this example, the blade edge 112 has serrations for cutting, ablating, abrading, or otherwise transforming bone or other tissue. In the alternative, the blade edge 112 is a continuous, planar arc, and sharpened along its entirety for cutting, ablating, abrading, or otherwise transforming bone or other tissue.

With continuing reference to FIG. 1, the cutting device 100 includes multiple static components 114 operable to move relative to the motion of the blade working body 108 in accordance with embodiments of the present disclosure. The static components 114 can support load (i.e. to help prevent blade binding), allow for free flow of bone debris, and create an air gap during cutting. The static components 114 can be positioned as shown or otherwise positioned or in any number along the working surface of the blade to prevent contact with bone or other material being cut or transformed. These components also decouple the motion of the blade working body 108 from the adjacent bone or other material being cut or transformed. The static components 114 provide sufficient circumferential clearance that they capture all blade excursion/motion produced by the blade working body 108. Specifically, the clearance around the static components 114 are designed to be larger than the desired excursion so as to ensure they can remain static during the cutting process relative to the dynamic motion of the blade working body 108.

FIG. 2 illustrates a top perspective view of the blade working body 108 and static components 114 shown in FIG. 1. Referring to FIG. 2, as shown an end of the blade working body 108 that opposes the blade edge 112 includes a clip portion 200 for attachment to another component of the cutting device 100. The clip portion 200 defines a rounded feature 202 that can fit to and pivot about a vertical member (not shown) for rotational movement about axis, indicated by a broken line 204.

FIGS. 3-5 illustrate tops views of the blade working body 108 shown in FIGS. 1 and 2 at different positions of operation for cutting or transforming a material, such as bone. Referring to FIGS. 3-5 it can be recognized that the blade working body 108 is at different positions with respect to static components 114. The blade edge 112 can be move back-and-forth generally in the directions indicated by double arrow 300. This back-and-forth motion occurs when the blade working body 108 pivot about axis 204. FIG. 3 depicts the blade working body 108 in a "neutral" position or approximately midway between an extent of movement to the left and to the right. FIG. 4 depicts the blade working body 108 at a position farthest to the right. FIG. 5 depicts the blade working body 108 at a position farthest to the left.

FIG. 6 illustrates a side, cross-sectional view of a portion of the working blade body 108 and one static component 114 as shown in FIGS. 1-5. The static component 114 comprises a flexible perimeter joint 600 and a load-sharing member 602. The flexible perimeter joint 600 encircles and is fitted to the load-sharing member 602. The flexible perimeter joint 600 is fitted into an aperture 604 formed within the working blade body 108 such that the joint 600 and the load-sharing member 602 are planar or substantially planar with respect to the plane of the working blade body 108. Particularly, the joint 600 is fitted within the aperture 604 such that the aperture functions as a socket to hold the static component 114. The static component 114 is thereby loosely held by the aperture 604. As a result of this configuration, the flexibile nature of the joint 600 mechanically separates the load-sharing member 602 from the surrounding blade body 108.

It is noted that the load-sharing member 602 has a height profile greater than the thickness of the blade body 108, such that the load-sharing member 602 extends perpendicularly some measure from both the top surface 110 and a bottom surface 606 of the blade working body 108. Although, it is noted that the components may have any other suitable height with respect to each other. In an example, a top end and a bottom end of the load-sharing member 602 are convex or curved in shape. The load-sharing member 602 and the flexible perimeter joint 600 can be one functional unit that move together and are not directly attached to the blade working body 108. Rather, their motion is constrained by the bounds of the countersunk aperture 604 in which they reside. Edges 608 of the aperture 604 are further countersunk in the surrounding blade body 108 such that the edge of the flexible perimeter joint 600 is the same height or subflush to the surface of the surrounding blade body 108. This allows the material being cut to more easily ride up on the static component. Specifically, as the blade working body 108 moves within the cutting plane the adjacent bone rides up on the static component 114. This can create an airgap to prevent direct conduction of heat to adjacent bone and allows for bone debris to flow away from the cutting site. It is believed that freely moving bone particulate matter can alleviate a significant amount of frictional forces that would otherwise be generated between the bone surfaces and the blade body 108. Airgaps are present circumferentially all around the flexible perimeter joint as well. Finally, this mechanism of the bone riding up on the static component 114 effectively supports loading on the top and bottom of the blade working body, which allows it to continue operation without frictional sliding interactions and prevents it from binding. It should be noted that fitting the flexible perimeter joint 600 to the load-sharing member 602 and fitting the flexible perimeter joint 600 within the aperture 604 can be accomplished using any variety of press-fit, slip-fit, snap-fit, adhesive, any combination thereof, or other suitable means. The flexible perimeter joint 600 can be made of a material having a low thermal conductivity including, but not limited to, rubber, silicone, or the like. The load-sharing member 602 can be made of a high strength medical grade material like stainless steel, cobalt chrome, and the like.

FIGS. 7-9 illustrate side views of a blade working body 108 at different positions cutting into a material 700 (e.g. bone) according to embodiments of the present disclosure. Referring to FIG. 7, the blade working body 108 is at an initial position for cutting into the material 700. At this position, the blade edge 112 has cut into the material to a distance such that the most distal static casing 114 has not reached the material 700.

Now turning to FIG. 8, the blade edge 112 has cut farther into the material 700 such that a portion 800 of the static casing 114 is within a gap 802 cut into the material 700. At the position shown in FIG. 8, the static casing 114 is carrying load from contact with the material 700 for alleviating strain on the blade working body 108. FIG. 9 shows the blade edge 112 having farther cut into the material 700 such that a large portion 900 of the static casing 114 is within the gap 802. In this position, a greater portion of the static casing 114 is carrying the load of the material 700.

It is noted that embodiments of the present disclosure are described as producing or having oscillatory saw blade movement or any other suitable source for motion. It is noted that in the alternative the movement may be any suitable type of movement produced by any suitable source (e.g., such as an ultrasonic transducer driving the blade through piezoelectric elements and smaller vibrations)). Further, cutting may be applied to any suitable material or technical field. Suitable mechanical sources could include anything from piezoceramics, electro-mechanical motors, user generated hand motion, etc. However, its important to note that all types of mechanisms can produce equivalent types of movements. These could include, but are not limited to, axial motion, bending motion, torsional motion, flexural motion, etc. It is also feasible that the source of mechanical motion can combine all of these modes of motion to create more complex movements. Regardless of the motion and/or the manner in which it is produced, there would be a resultant motion at the end of the functional device/blade edge. This motion would, under the claims of this patent, be captured within the bounds of the static casing which function to share load, decouple motion, and prevent heat transfer to the functional working surfaces. Examples include oscillating/sagittal/reciprocating medical bone cutting saws, medical rotary drills, medical rotary burs, construction hammer drills, construction rotary hammer, wood cutting axes, construction oscillating multi-tools, oscillating medical cast saws, cutting saws, etc. The principles of the claims presented in this patent could be applied to all of these devices with equivalently realized benefits.

While the embodiments have been described in connection with the various embodiments of the various figures, it is to be understood that other similar embodiments may be used, or modifications and additions may be made to the described embodiment for performing the same function without deviating therefrom. Therefore, the disclosed embodiments should not be limited to any single embodiment, but rather should be construed in breadth and scope in accordance with the appended claims.

The invention claimed is:
1. A cutting device comprising:
a working blade body having a top surface and a bottom surface, wherein the working blade body defines a plurality of apertures extending between the top surface and the bottom surface, wherein the working blade body defines a plurality of countersunk edge pairs that each substantially surround a corresponding one of the apertures at the top surface and the bottom surface, wherein the working blade body is substantially within a plane; and a plurality of static components each having a top portion and a bottom portion, wherein each static component is associated with one of the apertures and has a middle portion that is between the top portion and the bottom portion and positioned within the associated aperture, and wherein the top portion and the bottom portion of each static component are moveable within the countersunk edge pairs;

wherein each static component comprises a joint and load-sharing member, wherein the joint attaches the load-sharing member to the working blade body, and wherein each load-sharing member is defined to fit to a respective aperture and countersunk edge pairs with spacings such that a respective static component is moveable within the aperture and along the plane and moveable in a substantially less amount in directions outside of the plane for substantially maintaining movement of the static component with the plane of the working blade body.

2. The cutting device of claim 1, wherein the working blade body includes a blade edge positioned at a distal end.

3. The cutting device of claim 2, wherein the working blade body includes a proximal end, wherein the plurality of apertures and the associated static components are spaced apart between the proximal and distal ends of the working blade body.

4. The cutting device of claim 3, wherein the plurality of apertures and the associated static components are in substantial alignment.

5. The cutting device of claim 1, wherein each joint encircles its associated load-sharing member.

6. The cutting device of claim 1, wherein each joint is made of a rigid material.

7. The cutting device of claim 1, the top surface and the bottom surface are separated by a distance, and wherein a height of each static component is greater than the distance separating the top surface and the bottom surface.

8. The cutting device of claim 1, wherein the top portion and the bottom portion are each curved in shape.

9. The cutting device of claim 1, wherein each static component is substantially disk-like in shape.

10. The cutting device of claim 1, wherein each joint is substantially disk-like in shape.

11. The cutting device of claim 10, wherein each joint defines an aperture therein, and wherein the associated load-sharing member fits inside the aperture of the joint.

12. The cutting device of claim 1, wherein the working blade body is operatively attached to a source of movement for moving the working blade body.

13. A method comprising:
providing a cutting device comprising:
a working blade body having a top surface and a bottom surface, wherein the working blade body defines a plurality of apertures extending between the top surface and the bottom surface, wherein the working blade body defines a plurality of countersunk edge pairs that each substantially surround a corresponding one of the apertures at the top surface and the bottom surface, wherein the working blade body is substantially within a plane; and a plurality of static components each having a top portion and a bottom portion, wherein each static component is associated with one of the apertures and has a middle portion that is between the top portion and the bottom portion and positioned within the associated aperture, and wherein the top portion and the bottom portion of each static component are moveable within the countersunk edge pairs;

wherein each static component comprises a joint and load-sharing member, wherein the joint attaches the load-sharing member to the working blade body, and wherein each load-sharing member is defined to fit to a respective aperture and countersunk edge pairs with spacings such that a respective static component is moveable within the aperture and along the plane and moveable in a substantially less amount in directions outside of the plane for substantially maintaining movement of the static component with the plane of the working blade body, and applying a force to the working blade body for cutting a material.

14. The method of claim 13, wherein the working blade body includes a blade edge positioned at a distal end.

15. The method of claim 14, wherein the working blade body includes a proximal end, wherein the plurality of apertures and the associated static components are spaced apart between the proximal and distal ends of the working blade body.

* * * * *